United States Patent
El Giheny

(10) Patent No.: US 9,709,546 B2
(45) Date of Patent: Jul. 18, 2017

(54) PRESSURE-RATED CRYSTAL HOLDING DEVICE FOR USE IN A HIGH TEMPERATURE CRUDE CORROSIVITY TEST

(71) Applicant: Chevron U.S.A. Inc., San Ramon, CA (US)

(72) Inventor: Kyrolos Paul El Giheny, Richmond, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 91 days.

(21) Appl. No.: 14/807,029

(22) Filed: Jul. 23, 2015

(65) Prior Publication Data
US 2016/0169857 A1    Jun. 16, 2016

Related U.S. Application Data

(60) Provisional application No. 62/091,776, filed on Dec. 15, 2014.

(51) Int. Cl.

| | |
|---|---|
| *G01N 1/22* | (2006.01) |
| *B01L 9/00* | (2006.01) |
| *G01N 37/00* | (2006.01) |
| *B01L 3/00* | (2006.01) |
| *G01N 33/28* | (2006.01) |

(52) U.S. Cl.
CPC .................................. *G01N 33/28* (2013.01)

(58) Field of Classification Search
None
See application file for complete search history.

(56) References Cited

U.S. PATENT DOCUMENTS

| 5,706,840 A * | 1/1998 | Schneider | B08B 3/00 134/104.2 |
| 5,805,973 A * | 9/1998 | Coffinberry | B01J 19/02 123/668 |
| 5,910,216 A * | 6/1999 | Nakamura | C30B 15/30 117/218 |
| 7,717,568 B2 * | 5/2010 | Fujimori | B21D 53/08 29/890.035 |

(Continued)

OTHER PUBLICATIONS

Millichamp Jason et al, Application of a GaPO4 Crystal Microbalance for the Detection of Coke Formation in High-Temperature Reactors and Solid Oxide Fuel Cells; Ind. Eng. Chem. Res. 2011, 50, 8371-8375.*

*Primary Examiner* — Peter Macchiarolo
*Assistant Examiner* — Jermaine Jenkins
(74) *Attorney, Agent, or Firm* — Karen R. DiDomenicis

(57) ABSTRACT

Disclosed is a device for use in a test to measure the corrosivity of a high temperature hydrocarbon based fluid by determining areal mass density change from a metal layer deposited on a surface of a gallium orthophosphate ($GaPO_4$) crystal. The device includes a blind flange according to ASME B 16.5 having a peripheral bolt portion and a central portion. Bolt holes are present in the peripheral bolt portion of the blind flange for attaching the blind flange to a vessel. A hole through the central portion of the blind flange is provided to which a tube is securely attached at a first end. A second end of the tube is capable of holding the $GaPO_4$ crystal.

8 Claims, 1 Drawing Sheet

(56) References Cited

U.S. PATENT DOCUMENTS

| | | | |
|---|---|---|---|
| 8,033,164 B2* | 10/2011 | Dermody | G01N 17/043 |
| | | | 422/53 |
| 9,103,813 B2* | 8/2015 | Kusinski | G01N 17/02 |
| 9,140,679 B2* | 9/2015 | Kusinski | G01N 33/2823 |
| 2012/0078541 A1 | 3/2012 | Hesketh et al. | |
| 2014/0053779 A1* | 2/2014 | Martinson | C23C 16/45525 |
| | | | 118/723 R |

* cited by examiner

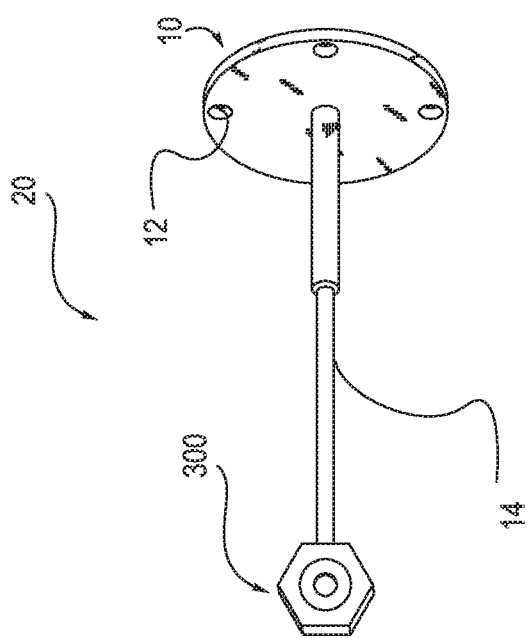

PRESSURE-RATED CRYSTAL HOLDING DEVICE FOR USE IN A HIGH TEMPERATURE CRUDE CORROSIVITY TEST

CROSS-REFERENCE TO RELATED APPLICATIONS

This application claims the benefit of U.S. Provisional Application No. 62/091,776, filed Dec. 15, 2014.

FIELD

The present disclosure relates to a laboratory test apparatus, more particularly a crystal holding device for use in a crude corrosivity test.

BACKGROUND

Because of market constraints, it is becoming economically more attractive to process highly acidic crudes such as acidic naphthenic crudes. However, it is well known that processing such acidic crudes can lead to various problems associated with naphthenic acid and other corrosion. Understanding the causes and extent of corrosion of various solutions on one or more of a range of materials is an important element of designing structures that resist such corrosion.

Analytical tools and methods of using these tools have been developed to assess corrosion and the corrosive potential of various solutions including highly acidic crudes such as acidic naphthenic crudes. Cost-effective, repeatable and reliable high temperature methods using crystal microbalance in relative mass change detection to determine the corrosion rates of metals in crudes have been developed.

Apparatus are needed to facilitate such methods, particularly apparatus able to withstand higher pressures encountered in test vessels at high temperatures.

SUMMARY

In one aspect, a device is provided for use in a test to measure the corrosivity of a high temperature hydrocarbon based fluid by determining areal mass density change from a metal layer deposited on a surface of a gallium orthophosphate ($GaPO_4$) crystal. The device includes a blind flange according to ASME B 16.5 having a peripheral bolt portion and a central portion. Bolt holes are present in the peripheral bolt portion of the blind flange for attaching the blind flange to a vessel. A hole through the central portion of the flange is provided to which a tube is securely attached at a first end. A second end of the tube is capable of attaching to a $GaPO_4$ crystal microbalance.

Other aspects, objects and advantages of the instant invention are apparent from the detailed description that follows.

DESCRIPTION OF THE DRAWINGS

These and other objects, features and advantages of the present invention will become better understood with reference to the following description, appended claims and accompanying drawings where:

FIG. 1 illustrates an exemplary device of the invention.

DEFINITIONS

The following terms will be used throughout the specification and will have the following meanings unless otherwise indicated.

The terms "comprises" and variations thereof do not have a limiting meaning where these terms appear in the description and claims.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "refinery feedstock" refers to natural and synthetic hydrocarbon-based fluids including but not limited to crude oil, synthetic crude biodegraded oils, petroleum products, intermediate streams such as residue, naphtha, cracked stock; refined products including gasoline, other fuels, and solvents. The term "petroleum products" refer to natural gas as well as crude oil, solid, and semi-solid hydrocarbon products including but not limited to tar sand, bitumen, etc.

Crudes, crude oils and crude blends are used interchangeably and each is intended to include both a single crude oil and blends of crude oils.

A "crystal microbalance" refers to a crystal having a surface that is at least partially coated with a deposited layer. The crystal microbalance generally finds use in measuring minute quantities or changes in quantities of a substance. Stress applied to the surface of a crystal generates voltage difference across the crystal. Correspondingly, providing an electric field causes a change the shape of the crystal. These corresponding effects are referred to as the piezoelectric effect and converse piezoelectric effect. Crystals also undergo a mass loading effect. Described by Sauerbrey in 1959, the mass loading effect describes the relationship between mass adsorbed on the surface of the crystal and the oscillating frequency of the crystal. A "crystal microbalance" is of use to determine the change in areal mass density adsorbed on the surface of a crystal by detecting the variation of the resonant oscillating frequency of the crystal. An exemplary "crystal microbalance" is of use to determine the loss of mass from a material attached to the surface of the crystal due to corrosion of that material.

An exemplary "crystal microbalance" system includes a crystal and an oscillating circuit. The oscillating circuit is coupled to the crystal for generating a resonant frequency of the crystal. Because the surface mass loading variation of the crystal is relatively small, the variation of the resonant frequency of the crystal is also relatively small. Thus, a crystal microbalance is generally integrated into a system that includes a means of detecting the signal and a means of amplifying the signal either before or after detection. As will be appreciated by those of skill in the art, detecting and amplifying components and configurations in which such structures are operatively linked to amplify a detectable or detected signal are well-known in the art and are applicable in the invention described herein.

"High temperature", as used herein refers to temperatures typically associated with refinery corrosion, i.e., from about 100° C. to above 400° C. The device and the associated procedure are capable of measuring corrosion rates at temperatures significantly higher than 400° C.

DETAILED DESCRIPTION

The present invention provides a device and a method for using the device in the crystal microbalance-based measurement of dynamic corrosion rates in refinery feedstocks and other high temperature or hydrocarbon-based fluids. The device is particularly suitable for use in tests to investigate the naphthenic acid corrosion of iron at high temperature.

Test methods have been proposed for the rapid determination of corrosion rates of a solid material suspended in a solution by measuring the frequency shift that accompanies mass change of a metal-coated gallium orthophosphate (also referred to as $GaPO_4$ or GAPO) crystal sample as the metal dissolves in the solution, thus providing reliable empirical data on the corrosivity of a certain solution in a matter of minutes. The ability to dynamically query the metal surface allows the in depth mechanistic study of the surface, which was subjected to corrosion. An exemplary solution is a refinery feedstock, e.g., a high temperature crude oil. The test methods are of particular use in the investigation of refinery corrosion. The test methods use a dual-chamber apparatus, including a first chamber in fluidic communication with a second chamber housing a $GaPO_4$ crystal microbalance having at least a portion of one surface coated with a metal, e.g., iron. The first and second chambers are fabricated from any conventional and convenient material. The material can be resistant to corrosion by the fluid that is being analyzed using the device. The first chamber is charged with the fluid (e.g., a high acid crude) to be tested, while the second chamber contains a metal coated $GaPO_4$ crystal microbalance in an inert atmosphere. The second chamber includes a means for stably retaining a first crystal microbalance (e.g., a bracket, clamp, septum, etc.), and the first crystal microbalance. The two chambers are heated concurrently, and once the target temperature is reached, the fluid is quickly transferred from the first chamber to the second chamber housing the metal-coated $GaPO_4$ crystal microbalance. At this point, the frequency response of the immersed crystal is recorded using a data acquisition system, e.g., a commercially available data acquisition system, for the duration of the test. Once the necessary data is gathered, the system can be shut down and cleaned out, and a new iron-coated crystal placed in the chamber for subsequent testing.

In one embodiment, a device for holding the metal-coated $GaPO_4$ crystal microbalance configured for measuring the corrosive properties of a hydrocarbon-based fluid according to the test methods described above is provided. Referring to FIG. 1, the device 20 includes a blind flange 10 having a peripheral bolt portion having a plurality of bolt holes 12 therethrough for attaching the blind flange to a vessel (not shown). The blind flange 10 can be made from a cast, forged, or plate material and can conform to ASME B16.5. The ASME B16.5 Pipe Flanges and Flange Fittings standard covers pressure-temperature ratings, materials, dimensions, tolerances, marking, testing, and methods of designating openings for pipe flanges and flanged fittings.

Attached to the central portion of the blind flange 10 is a tube 14 having a first end securely attached to the blind flange 10, e.g. by a welded joint, and a second end attaching to a crystal holder. The tube 14 attaches to a crystal holder 300 approximate the second end of the tube 14. The metal coating of the $GaPO_4$ crystal housed within the holder can be an iron layer.

In one embodiment, device 20 includes a data transmission cable (not shown) running through the tube 14.

The device 20 is configured to operate at high temperatures as that term is defined herein. Thus, an exemplary device is configured to operate within a temperature range of from about 180° C. to about 350° C. As will be apparent to those of skill in the art, the device will preferably also be fully functional within a temperature range of from about ambient (~25° C.) to about 350° C., or even above 350° C.

The metal-coated $GaPO_4$ crystal 300 can be configured with electrodes (not shown) on both sides of a thin disk of $GaPO_4$ crystal. In one embodiment, the layer of material deposited on a $GaPO_4$ crystal is a material that is relevant to and utilized in equipment for processing a refinery feedstock. Exemplary deposited layers on the $GaPO_4$ crystal include metals, e.g., carbon steel or other structural materials commonly used in a refinery. The deposited layer can be applied onto the $GaPO_4$ by any convenient method, e.g., sputter deposition and deposition by pulse laser ablation (PLD). In operation, the deposited layer (e.g., iron, carbon steel, etc.) is placed in contact with the fluid. The deposited layer can cover any useful amount of one surface of the $GaPO_4$ crystal.

Iron is the major component of carbon steel, which is the material of construction of most oil and gas equipment. It is known that iron is attacked by naphthenic acids present in the crudes, and that equipment is adversely impacted by the formation of soluble corrosion products, which are then released into the hydrocarbon stream. Thus, in one embodiment, the invention provides a $GaPO_4$ crystal with a deposited layer of iron on one surface of the $GaPO_4$ crystal.

The deposited layer can be applied onto the crystal by any convenient method, e.g., sputtering, vapor deposition, electroplating. In operation, the deposited layer (e.g., iron, carbon steel, etc.) is placed in contact with the corrosive solution, e.g., refinery feedstock.

It should be noted that only the components relevant to the disclosure are shown in the FIGURES, and that other components normally part of a laboratory test apparatus are not shown for simplicity.

Unless otherwise specified, the recitation of a genus of elements, materials or other components, from which an individual component or mixture of components can be selected, is intended to include all possible sub-generic combinations of the listed components and mixtures thereof. Also, "comprise," "include" and its variants, are intended to be non-limiting, such that recitation of items in a list is not to the exclusion of other like items that may also be useful in the materials, compositions, methods and systems of this invention.

From the above description, those skilled in the art will perceive improvements, changes and modifications, which are intended to be covered by the appended claims.

What is claimed is:

1. A device for use in a test to measure the corrosivity of a high temperature or hydrocarbon based fluid by determining areal mass density change from a metal layer deposited on a surface of a $GaPO_4$ crystal, wherein said device comprises:
   a. a blind flange having a peripheral bolt portion having a plurality of bolt holes therethrough for attaching the blind flange to a vessel and a central portion having a hole therethrough, wherein the blind flange has a pressure-temperature rating, a material, dimensions and tolerances conforming to standard ASME B 16.5; and
   b. a hollow tube having a first end securely attached to the hole through the central portion of the blind flange and a second end attached to a crystal holder for holding a $GaPO_4$ crystal microbalance.

2. The device of claim 1, further comprising a data transmission cable running through the hollow tube.

3. The device of claim 1, wherein the hollow tube is attached to the hole by a welded joint.

4. The device of claim 1, further comprising the $GaPO_4$ crystal microbalance having a metal layer deposited on the surface thereof in the crystal holder proximate the second end.

5. The device of claim 4, wherein the metal layer is an iron layer.

6. The device of claim 1, further comprising vessel wherein the blind flange is bolted to the vessel by means of bolts through the bolt holes.

7. The device of claim 5, wherein the device is capable of withstanding a test temperature of from 100° C. to 400° C.

8. The device of claim 1, wherein the high temperature hydrocarbon based fluid comprises crude oil.

\* \* \* \* \*